United States Patent [19]

Taylor et al.

[11] Patent Number: 4,871,746

[45] Date of Patent: Oct. 3, 1989

[54] N-[N-(TETRAHYDROPYRIDO[2,3-D]PYRIMIDINYLMETHYL)-AMINOMETHYLBENZOYL]GLUTAMIC ACID DERIVATIVES AS NEOPLASTIC GROWTH INHIBITORS

[75] Inventors: Edward C. Taylor, Princeton; James M. Hamby, Plainsboro, both of N.J.; Chuan Shih, Indianapolis, Ind.

[73] Assignees: The Trustees of Princeton University, Princeton, N.J.; Eli Lilly and Company, Indianapolis, Ind.

[21] Appl. No.: 200,136

[22] Filed: May 31, 1988

[51] Int. Cl.[4] .................. A61K 31/505; C07D 471/00
[52] U.S. Cl. ..................................... 514/303; 544/279
[58] Field of Search ........................ 544/279; 514/303

[56] References Cited

U.S. PATENT DOCUMENTS 4,596,805  6/1986  Jiang ................................. 544/279

OTHER PUBLICATIONS

Cutting, "Handbook of Pharmacology", Prentice-Hall, Norwalk, Connecticut, (1984), pp. 119–140.

*Primary Examiner*—Mary C. Lee
*Assistant Examiner*—Robert C. Whittenbaugh
*Attorney, Agent, or Firm*—Mathews, Woodbridge, Goebel, Pugh & Collins, P.A.

[57] ABSTRACT

N-[N-(Tetrahydropyrido[2,3-d]pyrimidinylmethyl) aminomethylbenzoyl]glutamic acid derivatives are antineoplastic agents with an effect on one or more enzymes which utilize metabolic derivatives of folic acid. The compounds can be prepared by allowing a protected aminomethylbenzoylglutamic acid derivative to react with 2-amino-4-hydroxy-6-formylpyrido[2,3-d]pyrimidine, reducing the intermediate Schiff base, and subjecting the intermediate to catalytic hydrogenation. A typical embodiment is (S,S) N-[N-(2-amino-4-hydroxy-5,6,7,8- tetrahydropyrido-[2,3-d]pyrimidin-6-ylmethyl)-4-aminomethylbenzoyl]-glutamic acid.

11 Claims, No Drawings

N-[N-(TETRAHYDROPYRIDO[2,3-D]PYRIMIDINYLMETHYL)-AMINOMETHYL-BENZOYL]GLUTAMIC ACID DERIVATIVES AS NEOPLASTIC GROWTH INHIBITORS

The present invention pertains to the individual diastereomers and to the diastereomeric mixture of glutamic acid derivatives of the formula:

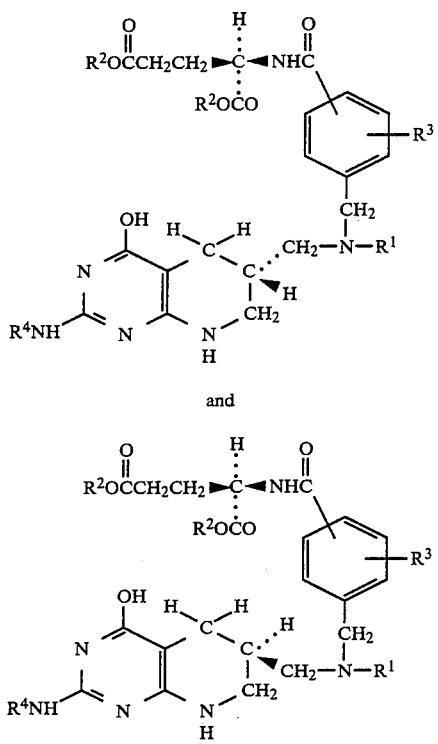

in which:

$R^1$ is hydrogen, alkyl of 1 to 6 carbon atoms, or alkanoyl of 1 to 6 carbon atoms;

$R^2$ is hydrogen or a carboxy protecting group;

$R^3$ *is hydrogen or halo;* and $R^4$ is hydrogen or an amino protecting group.

The compounds of Formula IA and IB have an inhibitory effect on one or more enzymes which utilize folic acid, and in particular metabolic derivatives of folic acid, as a substrate. The compounds thus can be used, alone or in combination, to inhibit the growth of those neoplasms which otherwise depend upon the enzymes so inhibited.

The invention also pertains to the pharmaceutically acceptable salts of the compounds of Formula IA and IB, to processes for the preparation of these compounds and their salts, to a method of combatting neoplastic growth in a mammal, and to pharmaceutical compositions containing these compounds and their salts.

The term alkyl as used herein denotes a straight or branched univalent aliphatic group of from 1 to 6 carbon atoms including methyl, ethyl, propyl, butyl, pentyl, hexyl, and the branched isomers thereof such as isopropyl, isobutyl, s.-butyl, t.-butyl, neopentyl, etc. Analogously, alkanoyl denotes a straight or branched univalent aliphatic acyl group of from 1 to 6 carbon atoms including formyl, acetyl, propionyl, butyryl, pivaloyl, etc.

When $R^3$ is halo, it can be chloro, bromo, iodo, or fluoro, preferably chloro or fluoro.

The protecting groups designated by $R^2$ and $R^4$ and utilized herein denote groups which generally are not found in the final therapeutic comounds but which are intentionally introduced during a portion of the synthesis to protect a group which otherwise might react in the course of chemical manipulations, thereafter being removed at a later stage of the synthesis. Since compounds bearing such protecting groups thus are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974.

A carboxy group can be protected as an ester group which is selectively removable under sufficiently mild conditions not to disrupt the desired structure of the molecule, especially a lower alkyl ester such as methyl or ethyl and particularly one which is branched at the 1-position such as t.-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group can also be protected in the form of an organic silyl group such as tri-lower alkylsilyl, as for example trimethylsilyloxycarbonyl.

Amino groups similarly can be protected as an amide utilizing an acyl group which is selectively removable under mild conditions, especially formyl, a lower alkanoyl group which is branched at the 1-position, particularly tertiary alkanoyl such as pivaloyl, or a lower alkanoyl group which is substituted in the 1-position, as for example trifluoroacetyl.

The compounds of the present invention often can be employed advantageously in the form of a pharmaceutically acceptable salt. Such forms, including hydrates thereof, are often crystalline and advantageous for forming solutions or formulating pharmaceutical compositions. Pharmaceutically acceptable salts with bases include those formed from the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts. The disodium salt is particularly advantageous.

The compounds of this invention can be prepared by allowing a protected aminomethylbenzoylglutamic acid derivative of the formula:

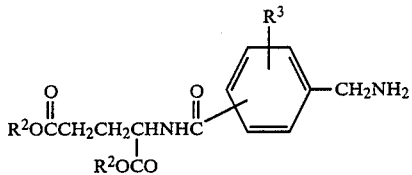

in which each $R^2$ is a carboxy protecting group; and $R^3$ is hydrogen or halo, with a 2-amino-4-hydroxy-6-formylpyrido[2,3-d]pyrimidine of the formula:

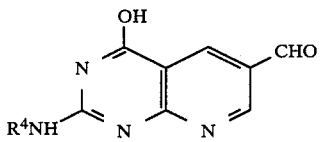

in which $R^4$ is amino protecting group. There is thus formed an intermediate Schiff base of the formula:

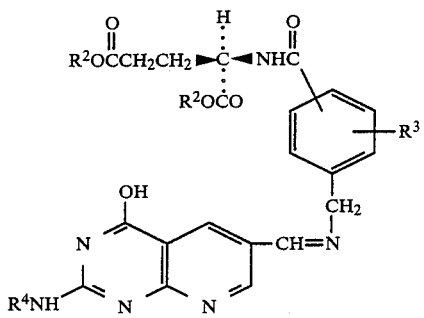

The Schiff base of Formula IV can be reduced in situ, as for example with a metal hydride such as a borohydride to yield the correspondingly protected N-[N-(2-amino-4-hydroxypyrido[2,3-d]pyrimidin-b 6-ylmethyl)-4-aminomethylbenzoyl)-glutamic acid derivative of Formula V:

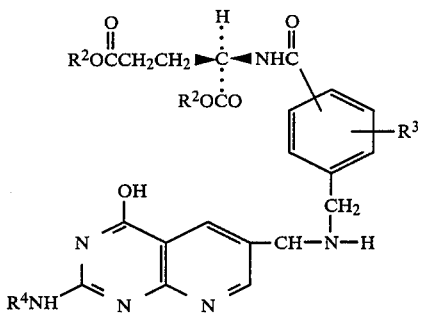

Upon catalytic hydrogenation of a compound of Formula V, there is obtained a mixture of diastereomers of Formulas IA and IB in which $R^1$ is hydrogen, $R^2$ is a carboxy protecting group, and $R^4$ is an amino protecting group. Suitable hydrogenation catalysts include noble metals and noble metal oxides such as palladium or platinum oxide, rhodium, and the foregoing on a support such as carbon or calcium oxide. Since there is some tendency for such hydrogenations to effect cleavage of the benzylic amine structure, the use of the milder rhodium on charcoal is preferred. Alternatively, a compound of Formula V can first be converted to an N-acylated derivative such as the corresponding N-formyl, N-acetyl, or N-trifluoroacetyl compound, the last being in the nature of a removable amino protecting group. With such additional protection, cleavage of the benzylic amine structure during hydrogenation is eliminated or minimized. Upon hydrogenation, there then is obtained a mixture of diastereomers of Formulas IA and IB in which $R^1$ is an acyl group, $R^2$ is a carboxy protecting group, and $R^4$ is an amino protecting group. Removal of the $R^2$ and $R^4$ protecting groups as by hydrolysis with base then yields a mixture of the diastereomeric compounds of Formulas IA and IB in which $R^2$ and $R^4$ are each hydrogen. As noted, when an easily hydrolysable N-acyl derivative such as an N-trifluoroacetyl compound is employed, this too is removed during hydrolysis of the $R^2$ and $R^4$ groups.

The mixture of the individual diastereomers depicted by Formulas IA and IB can be used therapeutically as such or can be separated mechanically as by chromatography. Alternatively, the individual diastereomers can be separated by forming diastereomeric salts with a chiral acid such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the individual diasteromeric bases, optionally repeating the process, so as obtain either or both substantially free of the other; i.e., in a form having an optical purity of >95%. This separation can be effected before or after removal of any protecting groups.

As noted, the compounds of this invention have an effect on one or more enzymes which utilize folic acid, and in particular metabolic derivatives of folic acid, as a substrate. The compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds also can be used to treat mycosis fungoides and psoriasis.

The compounds can be administered orally but preferably parenterally, alone or in combination with other therapeutic agents including other anti-neoplastic agents, steroids, etc., to a mammal suffering from neoplasm and in need of treatment. Parenteral routes of administration include intramuscular, intrathecal, intravenous or intra-arterial. Dosage regimens must be titrated to the particular neoplasm, the condition of the patient, and the response but generally doses will be from about 10 to about 100 mg/day for 5-10 days or single daily administration of 250-500 mg, repeated periodically; e.g. every 14 days. While having a low toxicity as compared to other antimetabolites now in use, a toxic response often can be eliminated by either or both of reducing the daily dosage or administering the compound on alternative days. Oral dosage forms include tablets and capsules containing from 1-10 mg of drug per unit dosage. Isotonic saline solutions containing 20-100 mg/ml can be used for parenteral administration.

The following examples will serve to further illustrate the invention. In the NMR data, "s" denotes singlet, "d" denotes quartet, "m" denotes multiplet, and "br" denotes a broad peak.

EXAMPLE 1

Diethyl N-[N-(2-Pivaloylamino-4-hydroxypyrido[2,3-d]-pyrimidin-6-ylmethyl)-4-aminomethylbenzoyl]-glutamate A mixture of 3.0 g (10.9 mmol) of 2-pivaloylamino-4-hydroxy-6-formylpyrido[2,3-d]pyrimidine, 4.47 g of diethyl N-(p-aminomethylbenzoyl)-L-glutamate hydrochloride (12.25 mmol), and 1.0 g (12.25 mmol) of sodium acetate in 70 mL of glacial acetic was stirred at 25° C. for 18 hours. To this solution was added 0.42 g (0.54 mL, 3.65 mmol) of borane-triethylamine complex. This mixture was stirred at 25° C. for 2 hours and the solvent then removed under reduced pressure. The residue was taken up in methylene chloride (200 mL), extracted once with water, and then twice with a saturated aqueous solution of sodium bicarbonate. The aqueous layers were combined and back extracted with methylene chloride. The organic layers were combined, dried over anhydrous magnesium sulfate, and the solvent removed under reduced pressure. The residue was recrystallized from ethyl acetate to give 3.4 g (52% yield) of diethyl N-[N-(2-pivaloylamino-4-hydroxypyrido[2,3-d]pyrimidin-6-ylmethyl)-4-aminomethylbenzoyl]-glutamate; mp 149°–151° C.; $^1$H NMR (Me$_2$Sod$_6$) delta 1.10–1.17 (m, 6H), 1.22 (s, 9H), 1.9–2.15 (m, 2H), 2.40 (t, 2H, J=7.4 Hz), 3.75 (s, 2H), 3.77 (s, 2H), 3.97–4.10 (m, 4H), 4.36–4.44 (m, 1H), 7.41–7.44 (m, 2H, AA'BB'), 7.80–7.83 (m, 2H, AA'BB'), 8.345 (d, 1H, J=2.09 Hz), 8.65 (d, 1H, J=7.38 Hz), 8.76 (d, 1H, J=2.09 Hz). Anal. Calcd for $C_{30}H_{38}N_6O_7$: C, 60.59; H, 6.44; N, 14.13. Found: C, 60.75; H, 6.68; N, 14.33.

In a similar fashion, diethyl N-[N-(2-pivaloylamino-4-hydroxypyrido[2,3-d]pyrimidin-6-ylmethyl)-3-aminomethylbenzoyl]-glutamate, diethyl N-[N-2-(2-pivaloylamino-4-hydroxypyrido[2,3-d]pyrimidin-6-ylmethyl)-3-fluoro-4-aminomethylbenzoyl]-glutamate, and diethyl N-[N-(2-pivaloylamino-4-hydroxypyrido[2,3-d]pyrimidin-6-ylmethyl)-2-chloro-4-aminoethylbenzoyl]-glutamate are prepared from diethyl N-(3-aminomethylbenzoyl)-glutamate, diethyl N-(3-fluoro-4-aminomethylbenzoyl)-glutamate, and diethyl N-(2-chloro-4-aminomethylbenzoyl)glutamate, respectively, and thereafter processed as exemplified in the following examples. The dialkyl aminomethylbenzoyl-glutamates starting materials can be synthesized from 3-aminomethylbenzoic acid, 3-fluoro-4-aminomethylbenzoic acid, and 2-chloro-4-aminomethylbenzoic acid according to the procedures described in Mol. Pharm., 8, 740–750.

EXAMPLE 2

Diethyl N-[N-(2-Pivaloylamino-4-hydroxypyrido[2,3-d]pyrimidin-6-ylmethyl)-N-formyl-4-aminomethylbenzoyl]-glutamate To a solution of 1.0 g. (1.7 mmol) of diethyl N-[N-(2-pivaloylamino-4-hydroxypyrido[2,3-d]pyrimidin-6-ylmethyl)-4-aminomethylbenzoyl]-glutamate in 10 mL of 98% formic acid was added 0.35 g. (0.33 mL, 3.5 mmol) of acetic anhydride. The mixture was stirred at 25° C. for 1 h. The solvent was removed under reduced pressure and the solid dissolved in methylene chloride and extracted twice with a saturated solution of sodium bicarbonate. The aqueous layers were back extracted with methylene chloride, and the organic layers combined and dried over anhydrous magnesium sulfate. The solvent was evaporated to dryness to give a quantitative yield of diethyl N-[N-(2-pivaloylamino-4-hydroxypyrido[2,3-d]pyrimidin-6-ylmethyl)-N-formyl-4-aminomethylbenzoyl]-glutamate which can be employed for further processing without further purification; $^1$H NMR (Me$_2$SO d$_6$) delta 1.11–1.18 (m, 6H), 1.24 (s, 9H), 1.9–2.15 (m, 2H), 2.39–2.44 (m, 2H), 4.39–4.42 (m, 3H), 4.53–4.55 (m, 2H), 7.21–7.44 and 7.34–7.37 (m, 2H, AA'BB'), 7.76–7.78 and 7.81–7.84 (m, 2H, AA'BB'), 8.12 and 8.13 (s, 1H), 8.61–8.78 (m, 2H).

EXAMPLE 3

Diethyl N-[N-(2-Pivaloylamino-4-hydroxypyrido[2,3-d]pyrimidin-6-ylmethyl)-N-trifluoroacetyl-4-aminomethylbenzoyl]-glutamate To a cold (0° C.) solution of 3.23 g. (5.43 mmol) of diethyl N-[N-(2-pivaloylamino-4-hydroxypyrido[2,3-d]pyrimidin-6-ylmethyl)-4-aminomethylbenzoyl]-glutamate in 50 mL of methylene chloride was added in a dropwise fashion over 10 min, 2.28 g. (10.86 mmol) of trifluoroacetic acid anhydride. The reaction mixture was allowed to attain room temperature and then stirred for 18 hours. One hundred milliliters of methylene chloride were added and the mixture then extracted three times with a saturated solution of sodium bicarbonate. The aqueous layers were back extracted with methylene chloride and the combined organic layers dried over anhydrous magnesium sulphate. The suspension was filtered and the filtrate evaporated under reduced pressure to give a quantitative yield of crude diethyl N-[N-(2-pivaloylamino-4-hydroxypyrido[2,3-d]pyrimidin-6-ylmethyl)-N-trifluoroacetyl-4-aminomethylbenzoyl]-glutamate which can be employed in the subsequent steps without further purification.

EXAMPLE 4

Diethyl N-[N-(2-Pivaloylamino-4-hydroxy-5,6,7,8-tetrahydropyrido[2,3-d]pyrimidin-6-ylmethyl)-N-formyl-4-aminomethylbenzoyl]-glutamate To a solution of 1.09 g. (0.17 mmol) of diethyl N-[N-(2-pivaloylamino-4-hydroxypyrido[2,3-d]pyrimidin-6-ylmethyl)-N-formyl-4-aminomethylbenzoyl]-glutamate in 50 mL of glacial acetic acid was added 164 mg of platinum oxide. The suspension was shaken in a Parr hydrogenation apparatus under an atmosphere (50 psi) of hydrogen at 25° C. for 3 hours. The reaction mixture was filtered through Celite and the filtrate evaporated under reduced pressure. The residue was dissolved in 100 mL of methylene chloride and extracted twice with a saturated solution of sodium bicarbonate. The aqueous layers were back extracted with 75 mL of methylene chloride and the organic layers combined, dried over anhydrous magnesium sulfate, and filtered. The filtrate was evaporated under reduced pressure and the residue chromatographed, eluting with 5% methanol in methylene chloride to give 0.8 g of diethyl N-[N-(2-pivaloylamino-4-hydroxy-5,6,7,8-tetrahydropyrido[2,3-d]pyrimidin-6-ylmethyl)-N-formyl-4-aminomethylbenzoyl]-glutamate (73% yield). An analytical sample was recrystallized from acetonitrile; mp 149°–151° C.; $^1$H NMR (Me$_2$SO d$_6$) delta 1.11–1.16 (m, 6H), 1.18 (s, 9H), 1.83–2.15 (m, 4H), 2.30∝2.47 (m, 3H), 2.79–3.20 (m, 4H), 3.98–4.11 (m, 4H), 4.36–4.43 (m, 1H), 4.53–4.54 (m, 2H), 6.40–6.51 (m, 1H), 7.33–7.36 (m, 2H, AA′BB′), 7.80–7.85 (m, 2H, AA′BB′), 8.11 and 8.38 (s, 1H), 8.67–8.73 (m, 1H). Anal. Calcd for $C_{31}H_{42}N_6O_8$: C, 59.41; H, 6.75; N, 13.41. Found: C, 59.14; H, 6.73; N, 13.64.

EXAMPLE 5

Diethyl N-[N-(2-Pivaloylamino-4-hydroxy-5,6,7,8-tetrahydropyrido[2,3-d]pyrimidin-6-ylmethyl)-N-trifluoroacetyl-4-aminomethylbenzoyl]-glutamate To 3.75 g. (5.43 mmol) of the product of Example 3, diethyl N-[N-(2-pivaloylamino-4-hydroxypyrido[2,3-d]pyrimidin-6-ylmethyl)-N-trifluoroacetyl-4-aminomethylbenzoyl]-glutamate, in 60 mL of glacial acetic acid are added 575 mg of platinum oxide. The suspension was hydrogenated in a Parr apparatus at 50 psi at 25° C. for 3 h. The reaction mixture was filtered through Celite and the solvent removed under reduced pressure. The residue was taken up in methylene chloride and extracted twice with a saturated solution of sodium bicarbonate and the organic layers dried over anhydrous magnesium sulfate and evaporated under reduced pressure. The residue was chromatographed, eluting with 5% methanol in methylene chloride to give 1.25 g (33% yield) of diethyl N-[N-(2-pivaloylamino-4-hydroxy-5,6,7,8-tetrahydropyrido[2,3-d]pyrimidin-6-ylmethyl)-N-trifluoroacetyl-4-aminomethylbenzoyl)-glutamate; $^1$H NMR (Me$_2$SO d$_6$) delta 1.11–1.15 (m, 6H), 1.33 (s, 9H), 1.6–2.1 (m, 6H), 2.28–2.33 (m, 2H), 3.07–3.18 (m, 1H), 3.97–4.10 (m, 4H), 4.10–4.20 (m, 1H), 6.64–6.67 (m, 1H), 8.03–8.06, (m, 1H).

EXAMPLE 6

N-[N-(2-Amino-4-hydroxy-5,6,7,8-tetrahydropyrido[2,3-d]pyrimidin-6-ylmethyl)-N-formyl-4-aminomethylbenzoyl]-glutamic Acid A solution of 0.5 g, (0.8 mmol) of diethyl N-[N-(2-pivaloylamino-4-hydroxy-5,6,7,8-tetrahydropyrido[2,3-d]pyrimidin-6-ylmethyl)-N-formyl-4-aminomethylbenzoyl]-glutamate in 0.1N NaOH was stirred at 25° C. for 5 days. The reaction mixture was filtered and the filtrate rendered acidic (pH 4) with 0.5N hydrochloric acid. The solid which formed after 1 h at 0° C. was collected, washed with water, and dried over P$_2$O$_5$ to give 0.26 g (67% yield) of N-[N-(2-amino-4-hydroxy-5,6,7,8-tetrahydropyrido[2,3-d]pyrimidin-6-ylmethyl)-N-formyl-4-aminomethylbenzoyl]-glutamic acid. An analytical sample was recrystallized from ethanol; mp 178° C. with gradually decomposition; $^1$H NMR (Me$_2$SO d$_6$) delta 1.75–2.23 (m, 5H), 2.2–2.42 (m, 3H), 2.65 ∝ 2.83 (m, 1H), 3.0–3.17 (m, 2H), 4.36–4.40 (m, 1H), 4.44–4.60 (m, 2H), 5.95 (s, 2H), 6.29 (s, 1H), 7.28–7.36 (m, 2H, AA′BB′), 7.69–7.92 (m, 2H, AA′BB′), 8.10 and 8.36 (s, 1H), 8.57 (t, 1H, J=7.78 Hz), 9.8 (br s, 1H). Anal. Calcd for $C_{22}H_{26}N_6O_7$: C, 54.32; H, 5.39; N, 17.28. Found: C, 54.67; H, 5.46; N, 17.02.

The IC$_{50}$ in whole cell human leukemia cell lines, CCRF-CEM, of N-[N-(2-amino-4-hydroxy-5,6,7,8-tetrahydropyrido[2,3-d]pyrimidin-6-ylmethyl)-N-formyl-4-aminomethylbenzoyl]-glutamic acid is 0.078 ug/mL.

EXAMPLE 7

Diethyl N-[N-(2-Pivaloylamino-4-hydroxy-5,6,7,8-tetrahydropyrido[2,3-d]pyrimidin-6-ylmethyl)-4-aminomethylbenzoyl]-glutamate To a solution of diethyl N-[N-(2-pivaloylamino-4-hydroxy[2,3-d]pyrimidin-6-ylmethyl)-4-aminomethylbenzoyl]-glutamate (0.37 g, 062 mmol) in glacial acetic acid was added 5% rhodium on charcoal (0.125 g) and the suspension shaken in a Parr apparatus under an atmosphere of hydrogen (50 psi) at 25° C. for 48 hours. The reaction mixture was filtered through celite to remove the catalyst and the filtrate evaporated under reduced pressure. The residue was dissolved in methylene chloride and extracted twice with a saturated aqueous solution of sodium bicarbonate. The reaction mixture was dried over anhydrous magnesium sulfate and the solvent removed under reduced pressure. The residue was recrystallized from ethyl acetate to give 0.233 g (37% yield) of diethyl N-[N-(2-pivaloylamino-4-hydroxy-5,6,7,8-tetrahydropyrido[2.3-d]pyrimidin-6-ylmethyl)-4-aminomethylbenzoyl]-glutamate; mp 146°–147° C.; $^1$H NMR (Me$_2$SO-d$_6$, exchanged D$_2$O) delta 1.09–1.15 (m, 6H), 1.15 (s, 9H), 1.90–2.17 (m, 4H), 2.40 (t, 2H, J=7.3 Hz), 2.50–2.60 (m, 1H), 2.75–2.85 (m, 1H), 2.85–2.97 (m, 1H), 3.96–4.07 (m, 4H), 4.10–4.11 (m, 2H), 4.37–4.43 (m, 1H), 7.55–7.57 (AA′BB′, 2H), 7.85–7.88 (AA′BB′, 2H), 8.76 (d, 1H, J=7.37 Hz). Anal. Calcd. for $C_{30}H_{42}N_6O_7$: C, 60.19; H, 7.07; N, 14.04. Found: C, 60.30; H, 6.85; N, 13.96.

EXAMPLE 8

Separation of Diethyl N-[N-(2-Pivaloylamino-4-hydroxy-5,6,7,8-tetrahydropyrido[2,3-d]pyrimidin-6-ylmethyl)-4-aminomethylbenzoyl]-glutamate Diastereomers A mixture of 1.0 g. of diethyl N-[N-(2-pivaloylamino-4-hydroxy-5,6,7,8-tetrahydropyrido[2,3-d]pyrimidin-6-ylmethyl)-4-aminomethylbenzoyl]-glutamate and 900 mg. of d(+)-camphorsulfonic acid in 50 mL of anhydrous ethanol is heated at reflux for 4 hours. After being allowed to cool, the mixture upon standing yields a solid which is collected by filtration and fractionally recrystallized several times from ethanol to yield the first diastereomer. Removal of the solvent from the mother liquor yields the other diastereomer which is recrystallized several times from ethanol until an optical purity >95% is obtained.

EXAMPLE 9

N-[N-(2-Amino-4-hydroxy-5,6,7,8-tetrahydropyrido[2,3-d]pyrimidin-6-ylmethyl)-4-aminomethylbenzoyl]-glutamic Acid A. A solution of 0.48 g, of diethyl N-[N-(2-pivaloylamino-4-hydroxy-5,6,7,8-tetrahydropyrido[2,3-d]-pyrimidin-6-ylmethyl)-N-trifluoroacetyl-4-aminomethylbenzoyl]-glutamate in 10 mL of 1N sodium hydroxide was stirred at 25° C. for 72 hours. To the reaction mixture was added charcoal and the suspension filtered through Celite. The filtrate was rendered acidic with acetic acid and stored at 0° C. for 4 hours. The solid which formed was collected, and washed sequentially with water, ethanol, and ether to give 0.241 g (76% yield) of N-[N-(2-amino-4-hydroxy-5,6,7,8-tetrahydropyrido[2,3-d]pyrimidin-6-ylmethyl)-4-aminomethylbenzoyl]-glutamic acid; mp 263° C. (dec); $^1$H NMR (Me$_2$SO d$_6$) delta 1.8–2.25 (m, 4H), 2.27 (t, 2H, J=6.95 Hz), 2.73–3.00 (m, 2H), 3.28–3.31 (m, 1H), 4.05 (s, 2H), 4.14 (s, 2H), 4.21 (s, 2H), 4.36–4.41 (m, 1H), 7.41–7.7.45 (m, 2H, AA'BB'), 7.80–7.82 (m, 2H, AA'BB'), 8.61 (s, 1H). Anal. Calcd for C$_{21}$H$_{26}$N$_6$O$_6$.H$_2$O: C, 53.95; H, 5.82; N, 17.97. Found: C, 54.07; H, 5.48; N, 17.76.

B. Similarly, from diethyl N-[N-(2-pivaloylamino-4-hydroxy-5,6,7,8-tetrahydropyrido[2,3-d]pyrimidin-6-ylmethyl)-4-aminomethylbenzoyl]-glutamate, there is obtained N-[N-(2-pivaloylamino-4-hydroxy-5,6,7,8-tetrahydropyrido[2,3-d]pyrimidin-6-ylmethyl)-4-aminomethylbenzoyl]-glutamic acid.

The IC$_{50}$ in whole cell human leukemia cell lines, CCRF-CEM, of N-[N-(2-amino-4-hydroxy-5,6,7,8-tetrahydropyrido[2,3-d]pyrimidin-6-ylmethyl)-4-aminomethylbenzoyl]-glutamic acid is 0.010 ug/mL.

In a similar fashion, N-[N-(2-pivaloylamino-4-hydroxy-5,6,7,8-tetrahydropyrido[2,3-d]pyrimidin-6-ylmethyl)-3-aminomethylbenzoyl]-glutamic acid, N-[N-(2-pivaloylamino-4-hydroxy-5,6,7,8-tetrahydropyrido[2,3-d]pyrimidin-6-ylmethyl)-3-fluoro-4-aminomethylbenzoyl]-glutamic acid, and N-[N-(2-pivaloylamino-4-hydroxy-5,6,7,8-tetrahydropyrido[2,3-d]pyrimidin-6-ylmethyl)-2-chloro-4-aminomethylbenzoyl]-glutamic acid are prepared from diethyl N-[N-(2-pivaloylamino-4-hydroxypyrido[2,3-d]pyrimidin-6-ylmethyl)-3-aminomethylbenzoyl]-glutamate, diethyl N-[N-(2-pivaloylamino-4-hydroxypyrido[2,3-d]pyrimidin-6-ylmethyl)-3-fluoro-4-aminomethylbenzoyl]-glutamate, and diethyl N-[N-(2-pivaloylamino-4-hydroxypyrido[2,3-d]pyrimidin-6-ylmethyl)-2-chloro-4-aminomethylbenzoyl]-glutamate, respectively, by analogous use of the procedures of the foregoing examples.

What is claimed is:

1. A compound selected from the group consisting of a glutamic acid derivative having the formula:

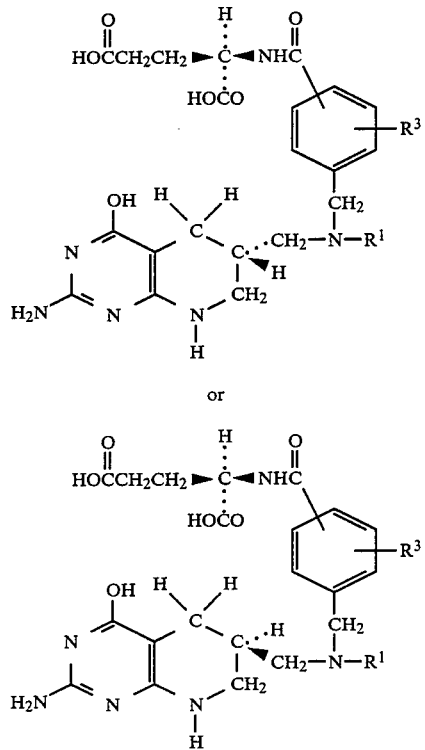

in which:

R$^1$ is hydrogen, alkyl of 1 to 6 carbon atoms, or alkanoyl of 1 to 6 carbon atoms; and R$^3$ is hydrogen or halo; and a pharmaceutically acceptable salt thereof.

2. A compound according to claim 1 wherein in said glutamic acid derivative R$^1$ is hydrogen, methyl, ethyl, formyl, or acetyl and R$^3$ is hydrogen, chloro, or fluoro.

3. A compound according to claim 2 wherein each of R$^1$ and R$^3$ is hydrogen, and the pharmaceutically acceptable salts thereof.

4. The compound according to claim 3 which is (S,S) N-[N-(2-amino-4-hydroxy-5,6,7,8-tetrahydropyrido[2,3-d]pyrimidin-6-ylmethyl)-4-aminomethylbenzoyl]-glutamic acid.

5. The compound according to claim 3 which is (R,S) N-[N-(2-amino-4-hydroxy-5,6,7,8-tetrahydropyrido[2,3-d]pyrimidin-6-ylmethyl)-4-aminomethylbenzoyl]-glutamic acid.

6. A compound according to claim 2 wherein R$^1$ is formyl and R$^3$ is hydrogen, and the pharmaceutically acceptable salts thereof.

7. The compound according to claim 6 which is (S,S) N-[N-formyl-N-(2-amino-4-hydroxy-5,6,7,8-tetrahydropyrido[2,3-d]pyrimidin-6-ylmethyl)-4-aminomethylbenzoyl]-glutamic acid.

8. The compound according to claim 6 which is (R,S) N-[N-formyl-N-(2-amino-4-hydroxy-5,6,7,8-tetrahydropyrido[2,3-d]pyrimidin-6-ylmethyl)-4-aminomethylbenzoyl]-glutamic acid.

9. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 1.

10. A pharmaceutical composition for inhibiting neoplastic growth in a mammal which growth is dependent on folic acid or a metabolic derivative of folic acid as a substrate, which comprises an amount of a compound according to claim 1 which upon administration to the mammal in a single or multiple dose regimen is effective to inhibit said growth, in combination with a pharmaceutically acceptable carrier.

11. A compound selected from the group consisting of a glutamic acid derivative having the formula:

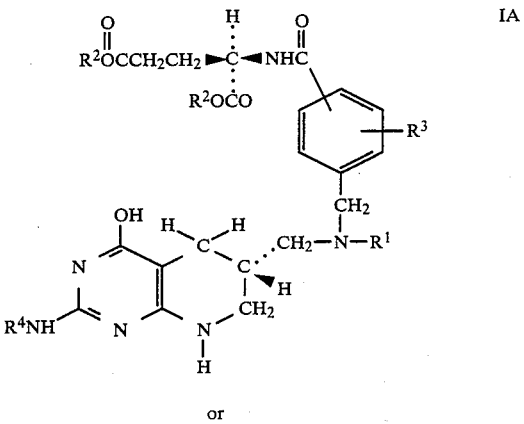

or

-continued

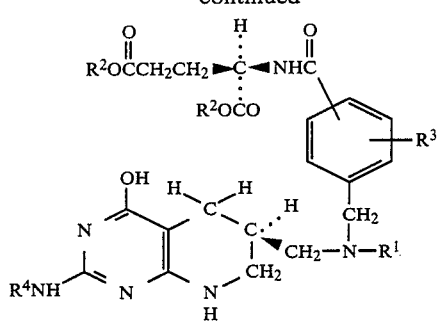

IB in which:

R[1] is hydrogen, alkyl of 1 to 6 carbon atoms, or alkanoyl of 1 to 6 carbon atoms;

R[2] is hydrogen or a carboxy protecting group selected from the group consisting of (a) a straight or branched lower alkyl ester which is unsubstituted or substituted in the 1- or 2-position with (i) lower alkoxy, (ii) lower alkylthio, (iii) halogen, (iv) phenyl which is unsubstituted or mono-, di- or tri-substituted with lower alkyl, lower alkoxy, hydroxy, halo, or nitro, or (v) aroyl, or (b) a silyl group;

R[3] is hydrogen or halo; and

R[4] is hydrogen or an unsubstituted or substituted lower alkanoyl amino protecting group, at least one of R[2] and R[4] being other than hydrogen.

* * * * *